United States Patent [19]
Coulter et al.

[11] Patent Number: 5,468,616
[45] Date of Patent: Nov. 21, 1995

[54] METHOD AND APPARATUS FOR RAPID MIXING OF SMALL VOLUMES FOR ENHANCING BIOLOGICAL REACTIONS

[75] Inventors: Wallace H. Coulter, Miami Springs; John D. Hollinger, Miami; Kenneth H. Kortright, Cooper City; Thomas Russell; Carlos Rodriguez, both of Miami; Ronald Paul, North Miami Beach, all of Fla.

[73] Assignee: Coulter Corporation, Miami, Fla.

[21] Appl. No.: 58,692

[22] Filed: Apr. 29, 1993

Related U.S. Application Data

[62] Division of Ser. No. 517,309, May 1, 1990, Pat. No. 5,238,812, which is a continuation of Ser. No. 25,337, Mar. 13, 1987, abandoned.

[51] Int. Cl.[6] .......................... C12Q 1/24; G01N 33/543
[52] U.S. Cl. .................. 435/7.2; 210/222; 366/219; 366/241; 435/7.24; 435/7.25; 435/30; 435/287.2; 436/526; 436/548; 436/808
[58] Field of Search ..................... 435/7.2, 7.24, 435/7.25, 30, 287, 316; 436/526, 548, 808; 210/222; 366/219, 241

[56] References Cited

U.S. PATENT DOCUMENTS

| | | | |
|---|---|---|---|
| 3,985,649 | 10/1976 | Eddleman | 430/177 |
| 4,267,234 | 5/1981 | Rembaum | 436/531 |
| 4,511,662 | 4/1985 | Baran et al. | 436/534 |
| 4,845,025 | 7/1989 | Lary et al. | 435/2 |
| 5,045,474 | 9/1991 | Becker et al. | 436/63 |
| 5,188,935 | 2/1993 | Leif et al. | 435/7.24 |
| 5,238,812 | 8/1993 | Coulter et al. | 435/7.2 |

FOREIGN PATENT DOCUMENTS 8203462  10/1982  WIPO .

OTHER PUBLICATIONS

Cotter et al, *Journ. Immunol.* 127, 1355–1360, 1981.

Brazenor et al, *Jour. Immunol. Methods.*, 2, 325–328, 1973.

*Primary Examiner*—David Saunders

[57] ABSTRACT

A method and apparatus for accelerating at least one definitive biological reaction including increasing the accuracy of determinations made therefrom. The reaction involves selected viable biological cells which are prepared in a small sample volume and rapidly mixed with microspheres having antibody specific at least to specific ones of the cells bound thereto. The microspheres can be magnetic and the bound cells can be magnetically removed to analyze the remaining blood cell populations. The microspheres can be introduced sequentially or simultaneously.

28 Claims, 5 Drawing Sheets

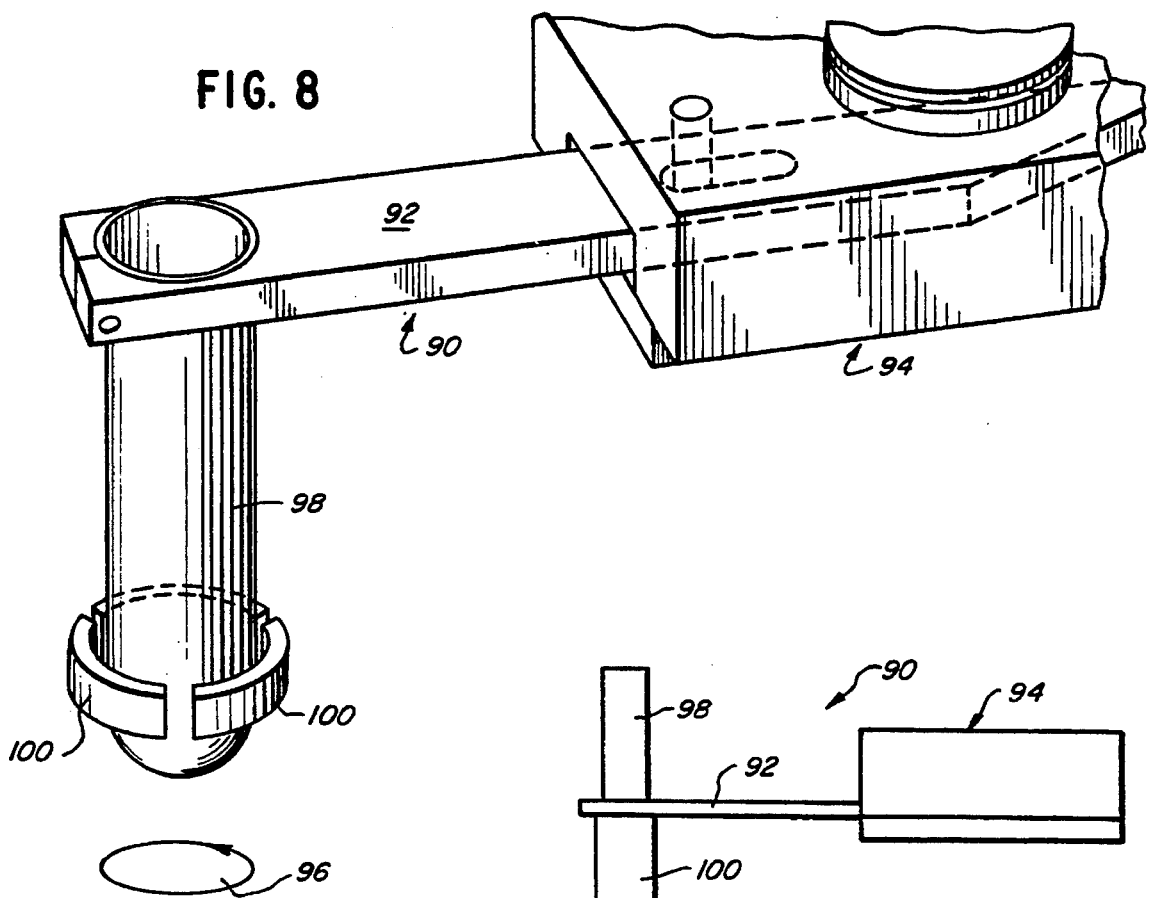
FIG. 8
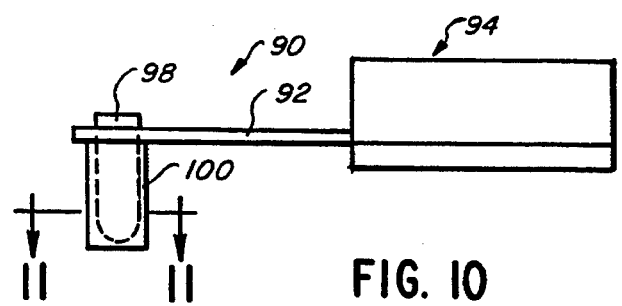
FIG. 9
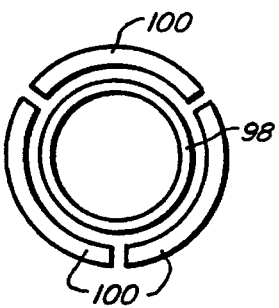
FIG. 11
FIG. 10

5,468,616

METHOD AND APPARATUS FOR RAPID MIXING OF SMALL VOLUMES FOR ENHANCING BIOLOGICAL REACTIONS

This application is a division of application Ser. No. 07/517,309, filed May 1, 1990, now U.S. Pat. No. 5,238,812, which is a continuation of application Ser. No. 07/025,337, filed Mar. 13, 1987, now abandoned.

BACKGROUND OF THE INVENTION

This invention is directed at significantly accelerating the rate of reaction and increasing the accuracy of making a qualitative and/or quantitative determination involving a biological or other fluid containing cells. More particularly, the invention is directed to a method and apparatus for accelerating the rate of an immunological reaction in which microspheres coated with at least one selected antibody are rapidly mixed with a sample containing the cells without significantly impairing the cellular properties of interest. The invention also can be useful in certain biochemical reaction determinations.

Immunological reactions of the type with which this invention is concerned include antigen/antibody reactions in which a microsphere, either magnetic or non-magnetic in character, is coated with the antibody, for instance, which will bind specifically with the antigen on a cell surface for making the desired determination. Such a reaction may include tagging or labelling the antigen for specific binding or can include labelling or tagging of a cell with respect to an antigen within the cell.

In the past, laboratory practice involving such mixing of labelled or tagged microspheres in a sample containing the cells' involved incubations from several minutes to several hours. One reason for such extended periods of time is attributable to the differences among the physical and chemical properties in the population of available microspheres for coating with the selected tag or label. Such extended time periods greatly restrict such procedures and prevent any type of rapid assay and particularly, application to automated techniques.

The prior art has attempted to optimize the time period of specific reactions by varying the volume and concentration of reactants together with the temperature at which the reaction is conducted and the desired mixing. Clearly, there are lower limits on how small a volume of the reaction mixture can be utilized. Further, increasing the temperature can denature the immunological reactants and strenuous mixing also can damage the cells.

Various types of mixing systems and methods also have been utilized in the prior art for particular immunological reactions. The prior art suggests agitating the mixture for extended periods of time which are undesirable for automated systems. Such automated systems are designed specifically for analyzing large numbers of samples per unit of time.

The method and apparatus embodying the invention successfully achieves optimum results in such immunological reactions by means of increased reaction rates which are unexpected and unusual in this field. Further, the invention enables a continuous mixing procedure which is especially conducive to automated systems. Further, the invention can be applied to accelerating mixing of reactants and formed bodies, such as bacteria, viruses and fungi which have specific properties of interest derived from biochemical reactions.

SUMMARY OF THE INVENTION

An improved method and apparatus for accelerating the rate of reaction of at least one immunological reaction, including increasing the accuracy of making a qualitative and/or quantitative determination involving a fluid suspension containing cells or formed bodies, such as bacteria, viruses and fungi. A small volume of a sample containing cells and microspheres tagged or labelled to bind specifically to determinant cites of cells or formed bodies are rapidly mixed for a period of time, which is significantly reduced compared to prior art practices. This rapid mixing still permits optimum determinations to be achieved without significantly impairing the cellular or the formed body's properties of interest.

The rapid mixing results achieved by the invention are especially useful for automated systems by reason of the reduced reaction time periods realized and the ability to mix continuously in an automated system. The microspheres utilized can be magnetic or non-magnetic in character.

BRIEF DESCRIPTION OF THE DRAWINGS

FIG. 8 is a perspective view of another mixer embodiment of the invention;

FIG. 9 is a side view of the mixer of FIG. 8;

FIG. 10 is a side view of the mixer of FIG. 8 illustrating another magnetic removal embodiment of the invention;

FIG. 11 is a top cross-sectional view of the magnetic removal embodiment of FIG. 10 taken along the lines 11—11 therein;

DESCRIPTION OF THE PREFERRED EMBODIMENTS

Figure 1:
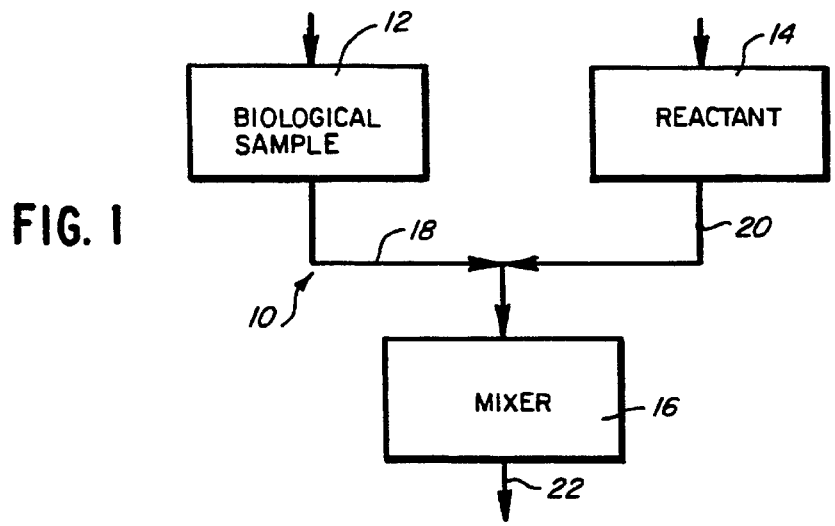
FIG. 1 is a schematic block diagram of one embodiment of the invention.

Referring to FIG. 1, one embodiment of the system embodying the invention is designated generally by the reference character 10. The system 10 includes a biological sample 12 containing cells (not illustrated), a reactant 14 including a material which will selectively react with cells, such as, a liquid or solid phase bound material and a mixer 16. The sample 12 can include whole blood, human body fluids containing cells, or other fluids containing formed bodies, such as bacteria, viruses and fungi.

The sample 12 is fed into the mixer 16 via a line 18. At least one reactant 14 also is added to the mixer 16 via a line 20. The reactant 14 can be a plurality of microspheres coated with an antibody specific to at least one type of cells desired to be bound to the microspheres (not illustrated). The reactant 14 further can be a combination of a preferential lyse and the coated microspheres.

One such preferential lyse and a quench which can be utilized therewith is disclosed in U.S. Pat. No. 5,155,044, which is a continuation of U.S. Ser. No. 07/317,147, filed Feb. 28, 1989, now abandoned which is a continuation of U.S. Ser. No. 07/025,303, filed Mar. 13, 1987, now abandoned, entitled METHOD AND REAGENT SYSTEM FOR ISOLATION, IDENTIFICATION AND/OR ANALYSIS OF LEUKOCYTES FROM WHOLE BLOOD SAMPLES, filed concurrently herewith, which is incorporated herein by reference.

The mixture of the sample 12 with the cells therein and the reactant 14 then rapidly is agitated in the mixer 16. The mixture is agitated for a significantly reduced time period, namely, generally greater than 2 seconds and less than 60 seconds; and preferably, for a whole blood sample, in the range of 5 to 15 seconds. The reduced period of mixing allows time to complete the reaction without significantly impairing the cellular properties of interest.

A critical factor in sample mixing is the selection of the volume of the sample 12 and the reactant 14 utilized. This volume is selected to be in the range of 50 to 700 microliters, and preferably for a whole blood sample, in the range of 100 to 200 microliters. The accelerated reaction speed is obtained without any increase in temperature. The mixing can be carried out at room temperature which avoids any possible deleterious effects on the cellular properties of interest.

Increased sample volumes can be accommodated within the parameters of the invention, such as, at least 1000 microliters, without significant increase in the time period of mixing.

After the short mixing period, the mixture can be discharged from the mixer 16 via a line 22 for a quantitative and/or qualitative analysis. For example, the cells of interest can be analyzed or can be further acted upon as illustrated in FIG. 2.

Figure 2:
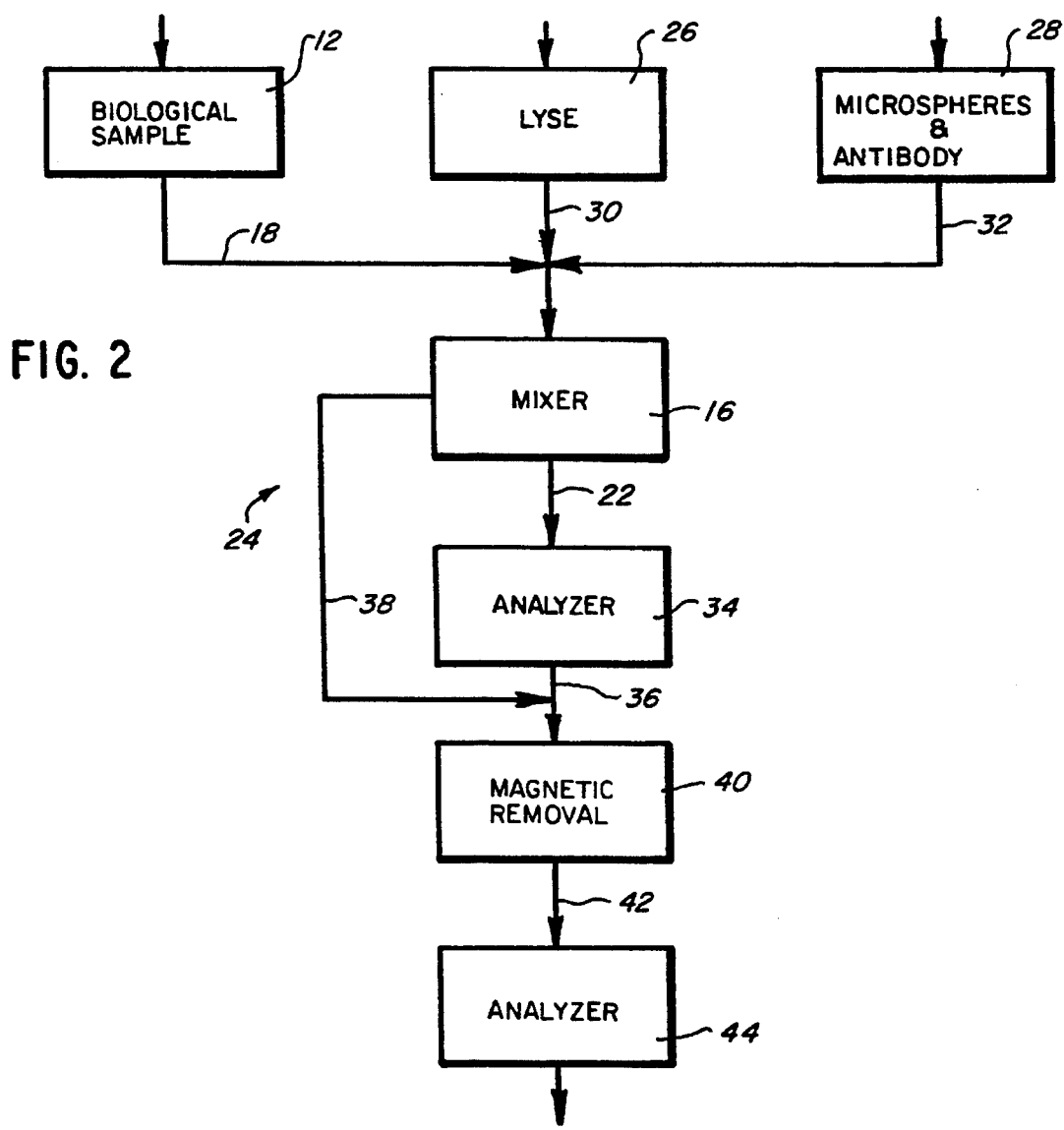
FIG. 2 is a schematic block diagram of a second embodiment of the invention.

A second mixing system 24 is illustrated in FIG. 2 (the same numerals are utilized for the corresponding elements in each of the Figs.). The biological sample 12 again can be fed to the mixer 16 via a line 18. The reactants are illustrated separately as a lyse 26 and a plurality of microspheres 28 with antibody bound thereto generally in a buffer, fed by respective lines 30 and 32 to the mixer 16.

As described with respect to FIG. 1, the mixture can be discharged from the mixer 16 via the line 22 and fed into a first analyzer 34, if desired. The mixture can be discharged from the analyzer 34 via a line 36 for further analysis or for the cells to be further acted upon in a similar manner as described herein. The analyzer 34 also could be coupled by a line 36' to another mixer with the other connections not illustrated.

The mixture also can be discharged via a line 38 to a magnetic removal device 40. At least some of the microspheres in that case will be formed of a magnetic material and the cells which are bound to them are captured in a magnetic field in the device 40. The remaining cells of interest then are discharged Via a line 42 to a second analyzer 44 for a further analysis.

Some specific analyzing systems in which the system 10 and the mixer 16 of the present invention can be utilized are disclosed in U.S. Ser. No. 07/587,646, filed Sep. 20, 1990, which is a continuation of U.S. Ser. No. 07/025,345, filed Mar. 13, 1987, and entitled AUTOMATED ANALYZER AND METHOD FOR SCREENING CELLS OR FORMED BODIES FOR ENUMERATION OF POPULATIONS EXPRESSING SELECTED CHARACTERISTICS, which is incorporated herein by reference.

Figure 3A:
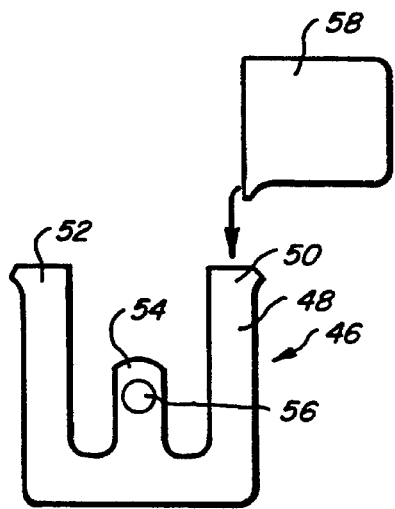
FIG. 3A and 3B are side views of one mixer embodiment of the invention, respectively in a fill and a pouring or discharging position.
Figure 3B:
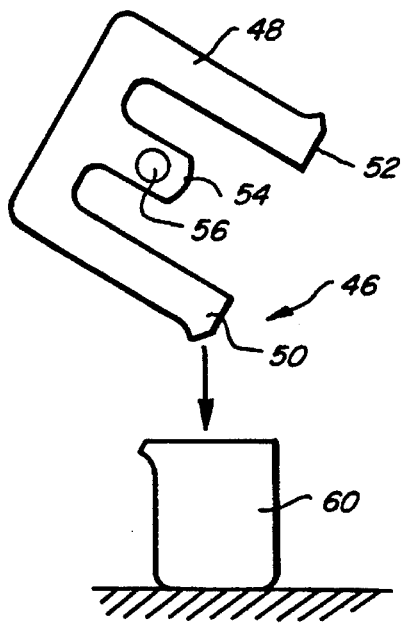

FIGS. 3A and 3B illustrate a first mixer embodiment 46 which can be utilized as the mixer 16. The mixer 46 includes a U-shaped type structure 48, which for example purposes, is illustrated as a U-tube type structure having a pair of open ends 50 and 52. The U-tube 48 includes a central arm 54, which includes an aperture 56 therein. The U-tube 48 is partially rotated or rocked generally around the axis of the aperture 56 to rapidly, but gently mix the mixture of the sample 12 and the reactant 14. As can be seen from FIGS. 3A and 3B, the aperture 56 remains in a relatively fixed position and hence easily can be utilized to add further liquids or reactants if desired, while the mixer 46 is in operation. Again, for illustration purposes, a beaker 58 is illustrated as being utilized to fill the mixer 46 and a beaker 60 is utilized to collect the mixed and reacted mixture. The aperture 56 need not necessarily be the port for receiving components. When the rocking mixing is interrupted with ports 50 and 52 in the fill position of FIG. 3A then the aperture 54 could be dispensed with, or the ports 50 and 52 can De coupled to an in line flow system.

Figure 4:
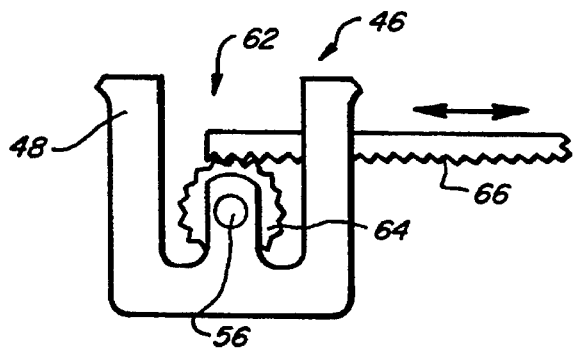
FIG. 4 is one drive embodiment for the mixer of FIGS. 3A and 3B.

FIG. 4 illustrates a first embodiment of a drive mechanism 62 which can be utilized to provide the rotational or rocking motion for the U-tube 48. The mechanism 62 includes a drive gear 64 which is mounted or otherwise affixed to the U-tube 48, such as, by adhesives or clamps (not illustrated), with a center of rotation axially aligned with the axis of the aperture 56. The gear 64 and hence the U-tube 48 is rotated by a serrated shaft 66, of which the serrations or teeth mate with the teeth of the gear 64. The U-tube 48 is rocked as a result of the movement of the shaft 66 in the directions illustrated by the arrow 68.

Figure 5:
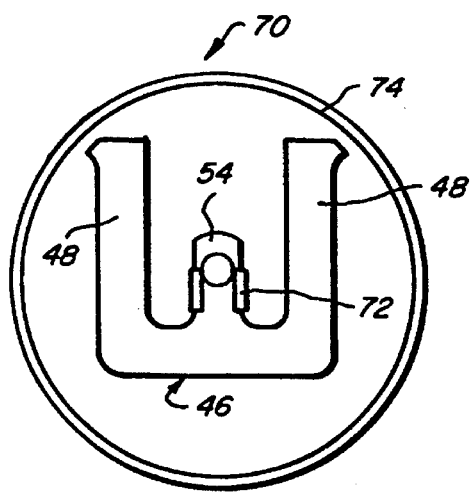
FIG. 5 is a second drive embodiment for the mixer of FIGS. 3A and 3B.

A second drive mechanism embodiment 70, is illustrated in FIG. 5. The mixer 46 and the U-tube 48 are mounted via the central arm 54 to a mounting clip 72. The mounting clip 72 is mounted or attached to the shaft (not illustrated) of a drive motor 74. The drive mechanism 70 accomplishes the rocking or rotation of the mixer 46 via the motor shaft and the clip 72, which motor and shaft preferably operate reversibly.

Figure 6A:
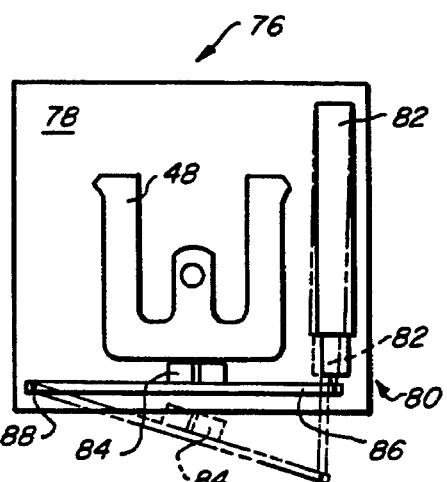
FIGS. 6A, 6B and 6C are side views of another mixer embodiment of the invention, similar to the mixer of FIGS. 3A and 3B, also illustrating one magnetic removal embodiment of the invention.
Figure 6B:
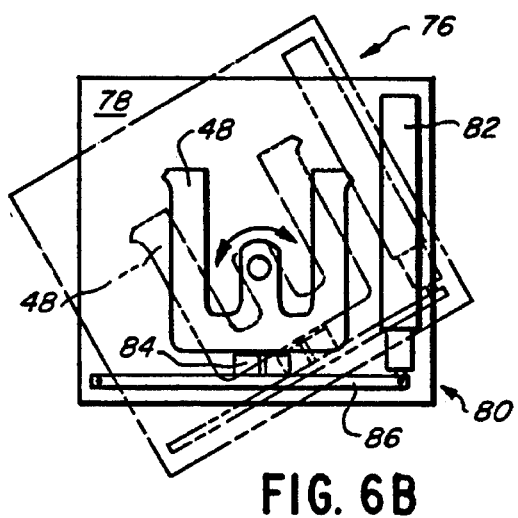
Figure 6C:
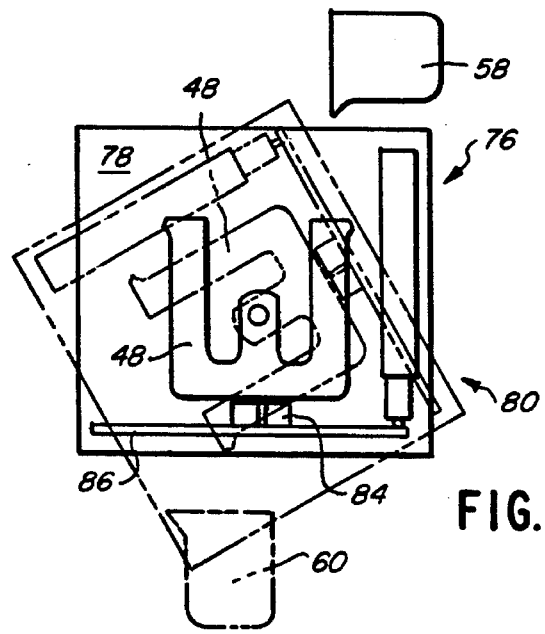

A mixer 76 with a magnetic separation mechanism is illustrated in FIGS. 6A–6C. The U-tube 48 is mounted or affixed to a mounting plate 78, which in turn is mounted onto the shaft (not illustrated) of a reversible motor to provide the rocking of the U-tube 48. A magnetic removal system 80 also is mounted onto the mounting plate 78 for rotation therewith.

The system 80 includes a pneumatic cylinder 82 shown in solid lines in its unactivated position in FIGS. 6A–6C. The cylinder 82 is shown in dotted lines in its activated position in FIG. 6A. In the unactivated position, the cylinder 82 retains a magnet 84 in close proximity to the bottom of the U-tube 48, which will capture any magnetic microspheres as the mixture passes by the magnet 84. The U-tube 48 then can be discharged into the collection beaker 60 without the cells captured or removed by the magnet 84 and the magnetic microspheres.

The magnet 84 is mounted on a pivotable shaft or arm 86, pivotable around a pivot point 88. The cylinder 82 is activated to pivot the shaft 86 and hence the magnet 84 away from the U-tube 48 to allow free movement of the magnetic microspheres. The cylinder 82 is activated in the initial mixing so that the microspheres can freely mix and bind the cells thereto. The cylinder 82 again would be activated to remove the magnetic microspheres from the U-tube 48. A sufficiently large magnetic field can be utilized so that all the magnetic microspheres will be captured without rocking the U-tube 48.

Figure 7:
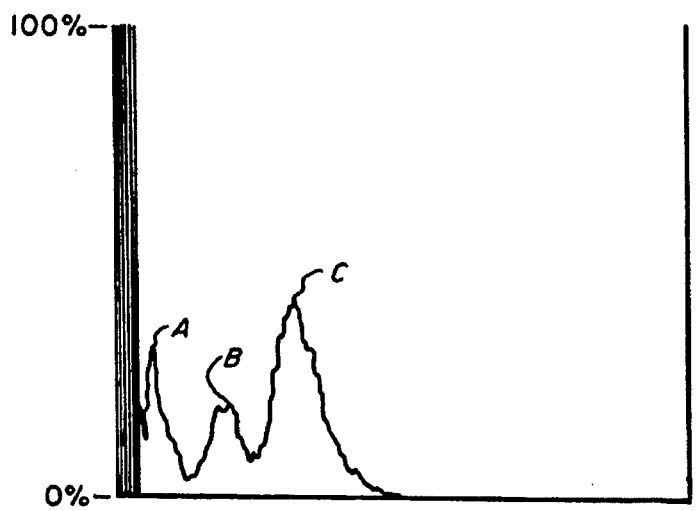
FIG. 7 is a graph of one set of results utilizing a mixer similar to that illustrated with respect to FIGS. 3A and 3B and FIGS. 6A–6C.

FIG. 7 illustrates one set of results obtained from a whole blood sample utilized with a mixing apparatus utilizing the U-tube 48. In this example, 40 microliters of magnetic microspheres with a red blood cell specific antibody bound thereto was combined with 150 microliters of buffer solution to form the reactant 14. In this example, the particular red blood cell specific antibody utilized is disclosed in application Ser. No. 799,489, filed Nov. 19, 1985, now U.S. Pat. No. 4,752,563, entitled MONOCLONAL ANTIBODY FOR RECOVERY OF LEUKOCYTES IN HUMAN PERIPHERAL BLOOD AND METHOD OF RECOVERY EMPLOYING SAID MONOCLONAL ANTIBODY, which is incorporated herein by reference. The biological sample 12 was a 10 microliter sample of whole blood which was added to the reactant 14. The U-tube 48 was rotated or rocked for 5 seconds outside of a magnetic field to bind the antibody and hence microspheres to the red blood cells. The magnetic 84 then was placed adjacent the U-tube 48 and the U-tube 48 was rocked an additional 10 seconds.

As above stated, if all the magnetic microspheres were placed within the magnetic field, then further rocking would not be necessary. The resulting sample was discharged and analyzed and the result was that greater than 99.5% of the red blood cells (A) were removed by the magnetic microspheres and the magnet 84. This allowed an analysis of the number of lymphocytes (B) and the granulocytes and monocytes (C) in the sample. As is well known, the red blood cells otherwise would block the detection of the lymphocytes, granulocytes and monocytes.

Another embodiment of mixer 90 generally is illustrated in FIGS. 8–10. The mixer 90 includes an arm 92 eccentrically mounted and driven by a rotating motor drive assembly 94. The arm 92 is driven in an eccentric motion as illustrated by the arrow 96. This motion provides a vortex mixing effect, thereby the mixture of liquid, cells and microspheres attempt to climb up the walls of a tube or vessel 98. The vortex effect provides a very efficient and rapid mixing of the mixture of the sample 12 and the reactant 14. As before, the mixer 90 can be operated first out of the magnetic field (FIG. 9) and then in the magnetic field (FIG. 10) to provide the magnetic separation. The magnetic separation also can be provided without operating the mixer 90.

In this embodiment, the magnetic field is provided by a plurality of bar magnets 100, which can be curved (FIG. 8) or straight (not illustrated). The magnets 100 can be moved relative to the tube 98 as disclosed with respect to FIGS. 6A–6C or the tube 98 can be moved relative to the magnets 100 as illustrated in FIGS. 9 and 10.

Figure 12:
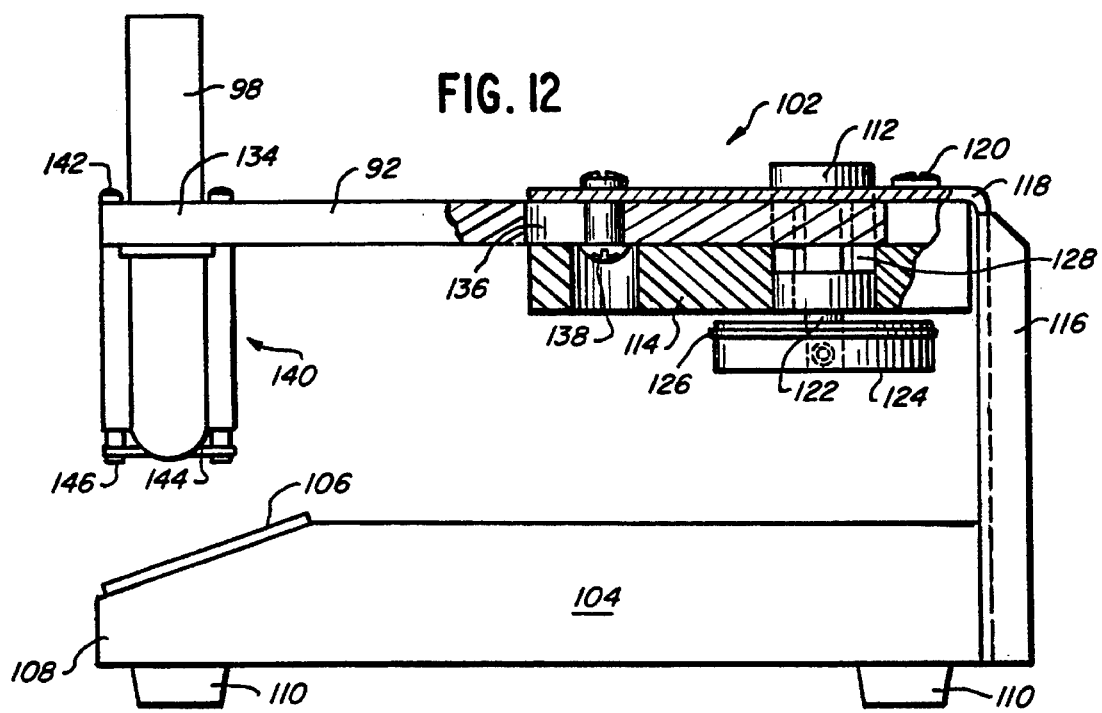
FIG. 12 is a side view of a detailed embodiment of the mixer of FIG. 8.
Figure 13:
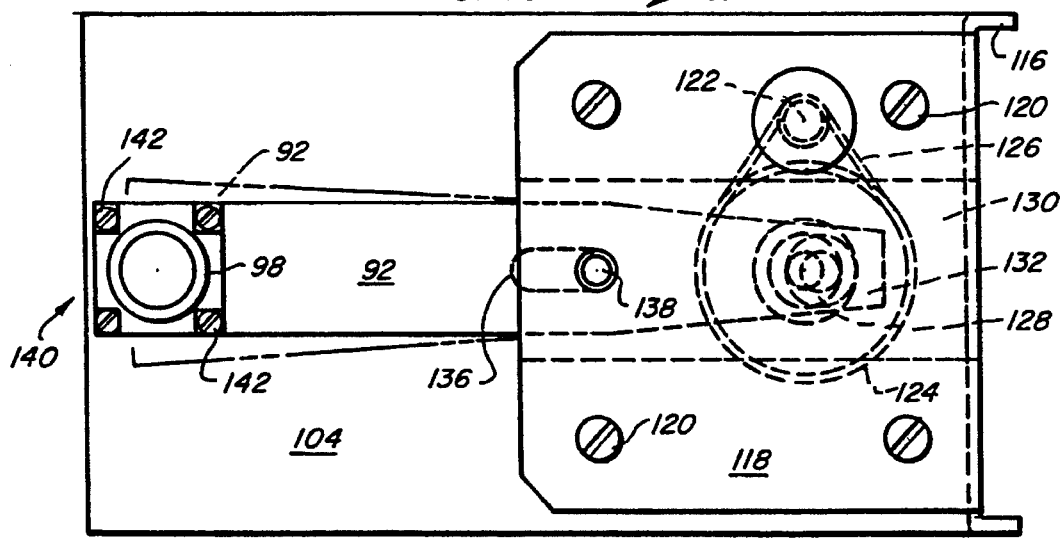
FIG. 13 is a top plan view of the mixer of FIG. 12.

A specific embodiment of the mixer 90 is a mixer 102 illustrated in FIGS. 12 and 13. The mixer 102 is illustrated mounted on a base 104, which can include a mirror 106 at one end 108 thereof. The mirror 106 can be utilized to view the mixture or absence thereof in the vessel 98. The base 104, which can be placed on any convenient surface, can include feet 110. The base 104 can be eliminated and the mixer 102 can be mounted in a system or to any other convenient surface, as desired.

A mixer drive motor 112 can be mounted to a motor block or base 114, which in turn is mounted to a support member 116. The member 116 can include an arm 118 through which a plurality of screws 120 are engaged into the block 114.

The motor 112 includes a drive shaft 122, which is rotatingly mounted in the block 114 and drives a pulley 124, such as by an O-ring drive belt 126. An eccentric pin 128 is mounted on the pulley 124 and extends into a passageway 130 in the block 114. The pin 128 is engaged in a first end 132 of the mixer arm 92.

A second end 134 of the mixer arm 92 holds the vessel 98. The arm 92 also includes a slot 136 which is slidingly engaged around a fixed pin 138 mounted in the block 114. As the eccentric pin 128 rotates, the first end 132 of the arm 92 moves back and forth (FIG. 13) to provide the mixing oscillation to the vessel 98 mounted on the second end 134.

The vessel 98 can be mounted or otherwise attached to the arm 92 by a holder 140 or other, preferably frictional, holding mechanism. The holder 140 can be mounted to the arm end 134 by a plurality of screws or bolts 142. The holder 140 can include a bottom vessel retainer 144, which can be retained by a similar plurality of bolts or screws 146. The particular dimensions and materials chosen are not critical and can vary as desired.

Figure 14:
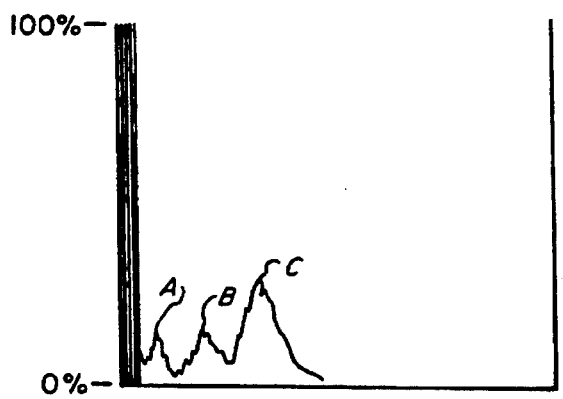
FIG. 14 is a graph of one set of results utilizing a mixer similar to that illustrated with respect to FIGS. 8–11.

The results of one whole blood sample reacted in the mixer 90, 102 are illustrated in FIG. 14. Forty microliters of red blood cell specific antibody coated magnetic microspheres was combined with 150 microliters of buffer solution to form the reactant 14. The same specific antibody utilized in the example illustrated in FIG. 7 was utilized in this example. The sample 12 was 10 microliters of a whole blood sample which was added to the reactant 14 in the vessel 98. The vessel 98 was vortexed or oscillated for 5 seconds to react the mixture. The magnetic field then was added for 10 seconds without operating the mixer 90 to separate the red blood cell bound magnetic microspheres from the remaining sample. The remaining sample then was analyzed and again a total of over 99.5% of the red blood cells (A) were removed. With the red blood cells (A) substantially all removed, the lymphocytes (B) and the granulocytes and monocytes (C) then were available for analysis.

Modification and variations of the present invention are possible in light of the above teachings. Other types of antibodies also can be utilized, for example a particular neutrophil (N) specific antibody which can be utilized is disclosed in MONOCLONAL ANTIBODY SPECIFIC TO NEUTROPHILS, U.S. Pat. No. 4,931,395, which is a continuation-in-part of parent application filed Dec. 8, 1986, U.S. Ser. No. 938,864. The magnetic field could be applied by electromagnetic devices. The mixer could be activated during application of the magnetic field if desired. Other mixer structures could be utilized, for example the U-shaped structure 48 could be an open structure similar to the structure of the beakers 58, 60. The addition of the fluids to one another can form part of a premixing action to aid in the speed of the reaction. It is therefore to be understood that within the scope of the appended claims, the invention may be practiced otherwise than as specifically described.

What is claimed and desired to be secured by Letters Patent of the United States is:

1. An apparatus for accelerating the rate of a reaction in a sample containing cells and into which sample a selected reactant is introduced for mixing to provide a suspension for making a quantitative and/or qualitative determination, said apparatus comprising:

means for introducing into a volume of sample of about 5 to 1,000 microliters containing a plurality of cells, at least one reactant including microspheres with an antibody bonded thereto preferential at least to some of said cells for providing a suspension suitable for making the determination;

means for mixing the resultant suspension of sample and reactant substantially at room temperature for a significantly reduced period of time on the order of approximately two to sixty seconds sufficient to accelerate the rate of reaction between the cells and reactant without impairing the cellular properties of interest or the accuracy of the determination; and means for performing immediately following said mixing at least one of separating some of said cells from said sample or determining a property of said cells without an incubation period.

2. The apparatus as defined in claim 1 wherein the sample volume is in the range of approximately 5 to 50 microliters.

3. The apparatus as defined in claim 1 wherein the sample volume is at least approximately 100 microliters.

4. The apparatus as defined in claim 1 wherein said time period is between approximately 5 to 15 seconds.

5. The apparatus as defined in claim 1 wherein said sample is a biological fluid.

6. The apparatus as defined in claim 1 wherein said reactant includes a preferential cell depleting agent.

7. The apparatus as defined in claim 1 wherein said sample is whole blood having red and white blood cell populations.

8. The apparatus as defined in claim 7 wherein said reactant includes at least a buffer.

9. The apparatus as defined in claim 7 further including means for introducing a preferential blood cell depleting agent.

10. The system as defined in claim 9 wherein said depleting agent is a preferential red blood cell lysing agent.

11. The apparatus as defined in claim 1 wherein said antibody is specific for red blood cells.

12. The apparatus as defined in claim 1 wherein said antibody is specific for neutrophils.

13. An apparatus for enhancing and accelerating at least one definitive biological reaction involving selected viable biological cells in a quantitative and/or qualitative determination, said apparatus comprising:

means for introducing into a small volume of a biological sample of about 5 to 1,000 microliters containing at least a plurality of biological cells, at least one reactant including microspheres with an antibody bonded thereto preferential at least to some of said cells, said biological sample including a whole blood sample or portion thereof including at least white blood cell populations therein;

means for mixing said mixture of sample and reactant for a significantly reduced period of time on the order of approximately two to sixty seconds sufficient to accelerate at least one of said definitive biological reactions without significantly impairing the biological properties of the cells of interest; and means for performing immediately following said mixing at least one of separating some of said biological cells from said sample or determining a property of said biological cells without an incubation period.

14. The apparatus as defined in claim 13 wherein said small volume is in the range of 100 to 200 microliters of liquid.

15. The apparatus as defined in claim 13 wherein said reduced period of time is in the range of 5 to 15 seconds.

16. The apparatus as defined in claim 13 wherein said biological sample includes a whole blood sample including at least a red blood cell population and white blood cell populations therein and including means for introducing a red blood cell preferential lyse.

17. The apparatus as defined in claim 16 wherein said mixing occurs substantially at room temperature.

18. The apparatus as defined in claim 13 wherein said antibody is specific to red blood cells and binds thereto.

19. The apparatus as defined in claim 18 wherein said microspheres are magnetic and including means for magnetically removing said bound red blood cells from said whole blood sample after said mixing.

20. The apparatus as defined in claim 13 wherein said antibody is specific to neutrophils and binds thereto.

21. The apparatus as defined in claim 20 wherein said microspheres are magnetic and including means for magnetically removing said bound neutrophils from said whole blood sample after said mixing.

22. The system as defined in claim 13 wherein said biological sample includes a whole blood sample including at least a red blood cell population and white blood cell populations therein.

23. The apparatus as defined in claim 22 wherein said rapid mixing occurs substantially at room temperature.

24. The apparatus as defined in claim 23 wherein said antibody is specific to red blood cells and binds thereto.

25. The apparatus as defined in claim 24 wherein said microspheres are magnetic and including means for magnetically removing said bound red blood cells from said whole blood sample after said rapid mixing.

26. The apparatus as defined in claim 22 wherein said antibody is specific to neutrophils and binds thereto.

27. The apparatus as defined in claim 26 wherein said microspheres are magnetic and including means for magnetically removing said bound neutrophils from said whole blood sample after said rapid mixing.

28. The apparatus as defined in claim 22 including means for removing said red blood cell population from said whole blood sample and then subtracting the neutrophil population percentage contribution from said white blood cell populations.

* * * * *